United States Patent
Säll et al.

(10) Patent No.: US 11,992,851 B2
(45) Date of Patent: May 28, 2024

(54) AEROSOL UNIT

(71) Applicant: SHL MEDICAL AG, Zug (CH)

(72) Inventors: Daniel Säll, Segeltorp (SE); Mattias Myrman, Tyresö (SE); Thomas Dietl, Falkenfels (DE)

(73) Assignee: SHL MEDICAL AG, Zug (CH)

( * ) Notice: Subject to any disclaimer, the term of this patent is extended or adjusted under 35 U.S.C. 154(b) by 476 days.

(21) Appl. No.: 17/294,246

(22) PCT Filed: Nov. 20, 2019

(86) PCT No.: PCT/EP2019/081909
§ 371 (c)(1),
(2) Date: May 14, 2021

(87) PCT Pub. No.: WO2020/120085
PCT Pub. Date: Jun. 18, 2020

(65) Prior Publication Data
US 2022/0001402 A1 Jan. 6, 2022

(30) Foreign Application Priority Data

Dec. 12, 2018 (EP) ..................................... 18212108

(51) Int. Cl.
*B05B 1/34* (2006.01)
*A61M 11/00* (2006.01)
(Continued)

(52) U.S. Cl.
CPC ......... *B05B 1/3402* (2018.08); *A61M 11/001* (2014.02); *A61M 11/007* (2014.02);
(Continued)

(58) Field of Classification Search
CPC ... B05B 1/3402; B05B 7/0012; B05B 7/0425; B05B 7/067; B05B 7/0815;
(Continued)

(56) References Cited

U.S. PATENT DOCUMENTS 5,586,550 A    12/1996   Ivri et al.
8,960,188 B2 *   2/2015   Bach .................. A61M 15/009
                                                               128/200.14
(Continued)

FOREIGN PATENT DOCUMENTS

EP          2676694 A2    12/2013
WO    2017/137252 A1    8/2017

OTHER PUBLICATIONS

International Search Report and Written Opinion for Int. App. No. PCT/EP2019/081909, mailed Feb. 12, 2020.

*Primary Examiner* — Frederick C Nicolas
(74) *Attorney, Agent, or Firm* — McDonnell Boehnen Hulbert & Berghoff LLP

(57) ABSTRACT

The present disclosure provides an aerosol unit for an aerosol dispenser. The aerosol unit includes an axially oriented body, having a distal inlet part and a proximal outlet part. The aerosol unit also includes a carrier member arranged in the body, transversally to the axis between the inlet part and the outlet part. The carrier member includes through-holes which place the inlet part in fluid communication with the outlet part, and the carrier member is insert-moulded into the body such that a contact surface between the carrier and the body forms an air-tight seal.

18 Claims, 8 Drawing Sheets

(51) Int. Cl.
*B05B 1/14* (2006.01)
*B05B 7/00* (2006.01)
*B05B 7/04* (2006.01)
*B05B 7/06* (2006.01)
*B05B 7/08* (2006.01)
*B05B 7/12* (2006.01)
*A61M 15/00* (2006.01)
*B05B 11/00* (2023.01)
*B05B 11/10* (2023.01)

(52) U.S. Cl.
CPC .............. *B05B 1/14* (2013.01); *B05B 7/0012* (2013.01); *B05B 7/0425* (2013.01); *B05B 7/0483* (2013.01); *B05B 7/067* (2013.01); *B05B 7/0815* (2013.01); *B05B 7/1209* (2013.01); *A61M 11/006* (2014.02); *A61M 15/0065* (2013.01); *A61M 2206/11* (2013.01); *A61M 2206/18* (2013.01); *A61M 2206/20* (2013.01); *A61M 2207/00* (2013.01); *B05B 11/0054* (2013.01); *B05B 11/1074* (2023.01); *B05B 11/109* (2023.01)

(58) Field of Classification Search
CPC . B05B 7/1209; B05B 11/1074; B05B 11/109; B05B 11/0054; B05B 1/14; B05B 7/0483; A61M 11/006; A61M 11/007; A61M 15/0065; A61M 2206/11; A61M 2206/18; A61M 2206/20; A61M 2207/00; A61M 11/001

See application file for complete search history.

(56) References Cited

U.S. PATENT DOCUMENTS

| | | | |
|---|---|---|---|
| 9,283,333 B2 * | 3/2016 | Schuy | A61M 11/00 |
| 9,682,202 B2 * | 6/2017 | Wachtel | A61M 15/0021 |
| 11,224,703 B2 * | 1/2022 | Kadel | A61M 11/003 |
| 11,376,375 B2 * | 7/2022 | Hijlkema | A61M 15/0085 |
| 2002/0162898 A1 | 11/2002 | Klimowicz et al. | |
| 2005/0183718 A1 | 8/2005 | Wuttke et al. | |
| 2013/0199521 A1 * | 8/2013 | Hausmann | A61M 11/007 128/200.23 |
| 2016/0095992 A1 | 4/2016 | Wachtel | |
| 2017/0281880 A1 | 10/2017 | Van Egmond et al. | |
| 2019/0038851 A1 * | 2/2019 | Hijlkema | A61M 11/005 |

* cited by examiner

AEROSOL UNIT

CROSS REFERENCE TO RELATED APPLICATIONS

The present application is a U.S. National Phase Application pursuant to 35 U.S.C. § 371 of International Application No. PCT/EP2019/081909 filed Nov. 20, 2019, which claims priority to European Patent Application No. 18212108.7 filed Dec. 12, 2018. The entire disclosure contents of these applications are herewith incorporated by reference into the present application.

TECHNICAL AREA

The present disclosure relates to an aerosol unit for an aerosol dispenser. In particular, it relates to an air-spray mix chamber having an integrated nozzle carrier.

BACKGROUND

There are many different kinds of aerosol dispensers on the market today. Aerosol dispensers comprising micro nozzles form an increasingly important and growing segment of the market. Micro nozzles may for instance be found in ink jet printing appliances, 3D printers, perfume containers and medicament delivery devices. Such nozzles comprise orifices for expelling the liquid spray, which orifices have diameters between 0.5 µm and 10 µm. To produce nozzles in the lower diameter range, the small dimensions require the orifices to be produced in micro technology processes, such as by etching channels in a semiconductor wafer, which wafer is thereafter diced into multiple individual micro nozzles. In order to increase the yield of each wafer, the nozzle dies are preferred to be made as small as possible, each typically having a surface area of 1 mm² or even smaller. Handling micro nozzle during manufacturing and assembly of an aerosol dispenser requires care in order not to damage the nozzle. A method to make handling easier is to mount the micro nozzle on a larger carrier member. Such nozzle carriers may then be mounted in an aerosol unit of an aerosol dispenser.

The aerosol unit of an aerosol dispenser is herein defined as the part of the dispenser where a fluid is formed into spray droplets and mixed with air or a carrier gas to form an aerosol. In the case of micro nozzles, it is important to control droplet dimensions to enable the aerosol to reach a designated delivery target, such as the lungs when the aerosol unit is comprised in an inhaler. It is therefore necessary to avoid the coalescence of the droplets or accidental deposition on surfaces of the dispenser. The mixing air or gas flows must be controlled in a manner which minimizes the coalescence or deposition of the droplets. To this end, flow channels are designed to provide the best flow with regard flow speed, turbulence, laminar flow, etc. A problem that often arises is the leakage of air or gas through gaps between components. Such leakage disturbs the engineered flow and reduces the performance of the aerosol dispenser.

US2017281880 discloses a method of mounting micro nozzle dies in a thermoplastic holder. The die is heated to thermally deform the plastic of the holder as the die is pushed into position. After the die and the plastic cool, the die is firmly mounted in the holder. However, it is difficult to position the die in the holder with a high degree of precision. In addition, the assembly of the holder with an air mixing chamber may give rise to leaking air flows.

Furthermore, some devices use a porous filter to create a laminar flow, parallel with the flow of aerosol, in order to prevent deposition on surfaces of the aerosol unit/dispenser. Since such filters are often soft or flexible, and clamped to the aerosol unit, they may give rise to leaking flows of air or gas along the edges.

The present disclosure presents a solution to the problems discussed above.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

In view of the foregoing, a general object of the present disclosure is to provide a aerosol unit for an aerosol dispenser, which aerosol unit comprises an axially oriented body, having a distal inlet part and a proximal outlet part, a carrier member arranged in the body, transversally to the axis between the inlet part and the outlet part, and wherein the carrier member comprises through-holes which place the inlet part in fluid communication with the outlet part, and wherein the carrier member is insert-moulded in the body such that a contact surface between the nozzle carrier and the body forms an air-tight seal.

The body may be made of plastic. Leaking air or gas flows are thus not a problem since the nozzle carrier is insert-moulded in the aerosol unit such that e.g. injection moulded plastic material of the body of the aerosol unit solidifies into sealing contact with surfaces of the carrier member.

The through-holes of the carrier member may be arranged so that a protective fluid flow, such as flow of air or gas, may be generated in the outlet part, which flow prevents droplets of the aerosol from depositing on surfaces of the aerosol unit. The protective fluid flow may be an air flow generated by inhalation of a user of the aerosol unit.

According to one aspect of the disclosure the carrier member comprises a micro nozzle mounted on the carrier member, through which micro nozzle a pressurised fluid product may be sprayed.

The micro nozzle comprises orifices having diameters between 0.5 µm and 10 µm. A fluid, e.g. a liquid, may be pressurised in a container or chamber and be forced through the orifices from a distal side thereof. Depending on viscosity, pressure and orifice diameters, the fluid exiting the orifices on a proximal side will form a spray in the form of Rayleigh droplet trains.

According to one aspect of the disclosure the carrier member is formed of a sheet metal member.

A carrier member, in the form of a metal strip having through-holes, is easily produced and may be conveniently cut from a piece of sheet metal and assembled with a micro nozzle before placing the carrier member, comprising the micro nozzle, in the aerosol unit moulding tool for insert-moulding. The through-holes of a metal strip may be accurately and precisely dimensioned and laid out, in contrast to through-holes of a plastic component, which would suffer from large tolerance variations. In addition, it may be very difficult to create through-holes having a diameter smaller than 0.5 mm in a plastic moulding process.

According to one aspect of the disclosure the outlet part comprises an outer fluid flow channel and an inner fluid flow channel, wherein the outer fluid flow channel and the inner fluid flow channel are generally coaxially arranged, and wherein a turbulence structure extends proximally a distance from the carrier member, between the inner fluid flow channel and the outer fluid flow channel.

According to one aspect of the disclosure the micro nozzle is aligned with the inner fluid flow channel and places the inner fluid flow channel in fluid communication with the distal part.

The protective fluid flow in the outer fluid flow channel is provided by means of the through-holes of the nozzle carrier radially outside the turbulence structure. The protective flow is generated by air inhaled by a user, or by pressurised gas from a separate gas source. The outer fluid flow channel guides the protective flow and the inner fluid flow channel guides the generated spray in the form of Rayleigh droplet trains mixed with fluid, e.g. air.

The micro nozzle is arranged in connection with the inner fluid flow channel to place the inner fluid flow channel in fluid communication with the distal part. Pressurised fluid may thus be forced through the orifices of the micro nozzle and into the inner fluid flow channel, where the expelled fluid forms a spray by break-up of Rayleigh droplet trains.

According to one aspect of the disclosure the wall element is arranged radially outside the inner fluid flow channel and extends proximally a distance from the carrier member, such that the outer fluid flow channel is located outside the turbulence structure, and the through-holes are located outside the turbulence structure.

The turbulence structure surrounds a mix area having turbulence ports for creating turbulence in the area where the liquid product is expelled as a spray. The outer fluid flow channel serves to create a "protective" flow outside the turbulence structure, to prevent droplets from depositing on the wall element or on surfaces of an outlet port, such as a mouthpiece.

According to one aspect of the disclosure the outer fluid flow channel and the inner fluid flow channel merge at a proximal end of the turbulence structure to form an outlet fluid flow channel.

The outlet fluid flow channel may be formed by the wall element, extending proximally from the carrier member. At the proximal end of the outlet fluid flow channel, an aerosol is expelled from the aerosol unit by the mixed gas or air flow.

According to one aspect of the disclosure the proximal part is configured to receive an outlet port of an aerosol dispenser.

The outlet port, such as a mouthpiece for inhalation, an eye piece for eye spray applications, a funnel, etc., may be attached to the proximal part, e.g. to the wall element, by any conventional means. Among the examples are threaded connections, bayonet couplings, glue, friction-fit, snap-fit, etc. The aerosol unit is thus easy to adapt for existing aerosol dispensers as it may be configured as an interface between e.g. a mouthpiece and a drive unit comprising a liquid product.

According to one aspect of the disclosure the proximal part is an outlet port of an aerosol dispenser.

The proximal part, e.g. the part comprising the wall element, may be configured as an outlet port of an aerosol dispenser, according to any of the examples above, and more. As such there is no need for an additional component. Therefore, the aerodynamic properties of the outlet port may be more accurately calculated for the single component, as compared to multiple components, which multiple components lead to longer tolerance chains and a risk of misattachment and/or leakage air flows.

According to one aspect of the disclosure the inlet part comprises a first connecting element for connecting the aerosol unit to a chamber containing a fluid product, which chamber may be pressurised such that the fluid product is pressurised and expelled through the micro nozzle as a spray.

According to one aspect of the disclosure the chamber is a metered dose chamber of aerosol dispenser.

According to one aspect of the disclosure the connecting member is a luer lock coupling, a luer slip coupling, a thread, an O-ring, a gasket, a bayonet coupling or a cone-to-cone coupling for sealingly connecting the aerosol unit to a primary package under working pressure.

Luer couplings are standardised connections for primary packages, e.g. containers such as cartridges and syringes. The aerosol unit may be configured to be connected to containers through such standard couplings, to provide a liquid-tight seal, under working pressure, with the container. However, other liquid-tight sealing connections, e.g. as mentioned above, are equally possible.

According to one aspect of the disclosure the inlet part comprises a second connecting element configured to connect the aerosol unit to a drive unit arranged to pressurise the fluid product in the chamber.

The aerosol unit may be directly attached to the drive unit, which drive unit comprises components and mechanisms for pressurising a fluid product in a container and driving the pressurised fluid product through the micro nozzle. As such, the aerosol unit may be easily adapted to work with various drive units.

According to one aspect of the disclosure the aerosol unit comprises a turbulence duct comprising a covered flow channel from an exterior of the aerosol unit to the inner fluid flow channel.

The turbulence duct is covered so that the protective flow in the outer fluid flow channel is not degraded by disturbance from a flow into the inner fluid flow channel and vice versa. With a covered channel it is also possible to divide the fluid (air) flows as appropriate into a turbulence flow directed to the inner fluid flow channel and a protective flow for the outer fluid flow channel.

According to one aspect of the disclosure the turbulence duct opens into the inner fluid flow channel through turbulence ports comprised in the turbulence structure.

The turbulence ports serve to direct fluid (air) flow to mix the Rayleigh droplet trains with air, creating the aerosol.

According to a further main object of the present disclosure, an aerosol dispenser comprises an aerosol unit, as described by any of the aspects above.

The present aerosol unit may be simply and reliably manufactured because the nozzle carrier may be placed in the moulding tool and integrated into the body of the aerosol unit, which eliminates leakage air/gas flows and results in shorter tolerance chains due to fewer assembled components.

BRIEF DESCRIPTION OF DRAWINGS

In the following detailed description of the present disclosure, reference will be made to the accompanying drawings, of which

DETAILED DESCRIPTION

The novel features of the present disclosure will now be described more fully hereinafter with reference to the accompanying drawings, in which exemplifying embodiments are shown. The novel features may, however, be embodied in many different forms and should not be construed as limited to the embodiments set forth herein; rather, these embodiments are provided by way of example so that this disclosure will be thorough and complete, and will fully convey the scope of the novel features to those skilled in the art. Like numbers refer to like elements throughout the description.

Figure 1:
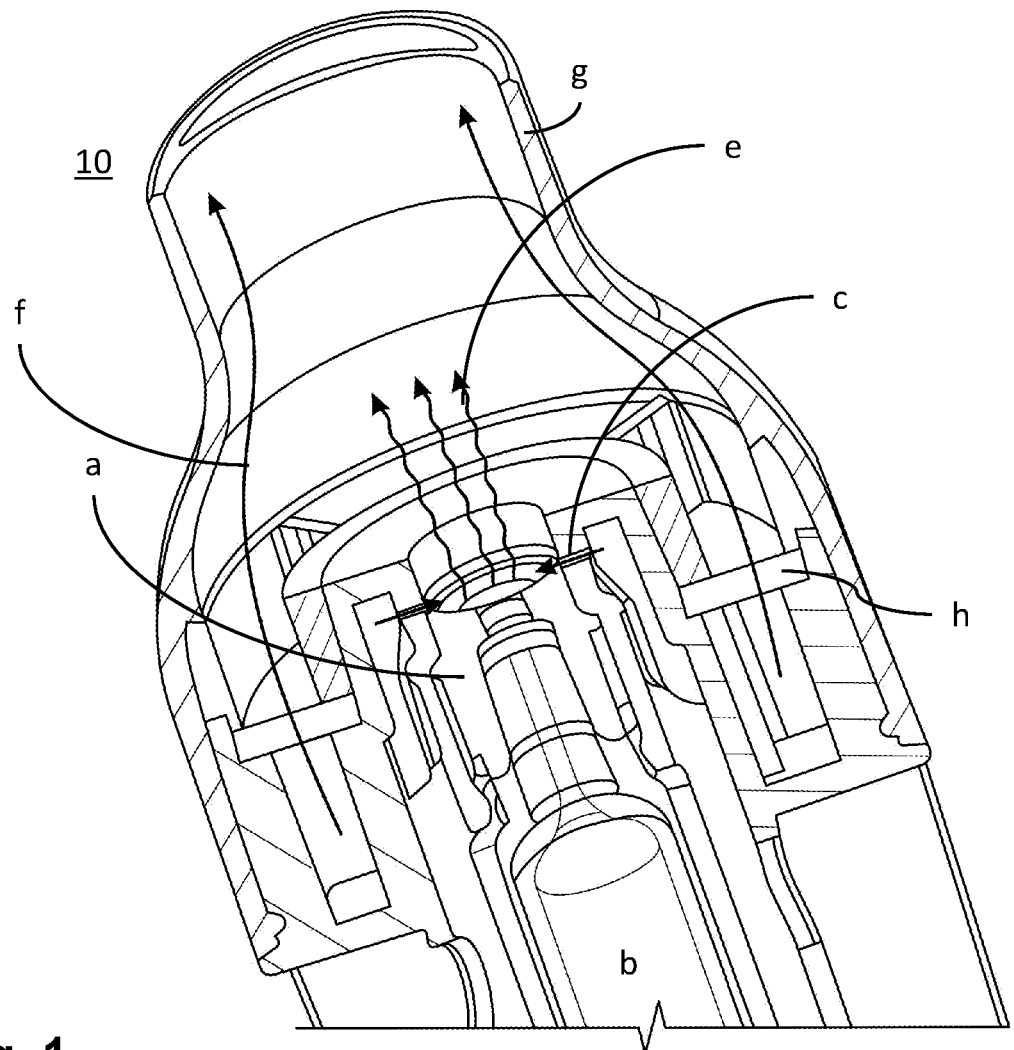
FIG. 1 shows a perspective cross-sectional view of a proximal part of a prior art inhalation device.

A proximal part of a known inhalation device is shown in FIG. 1. A nozzle unit a, comprising a micro nozzle, is arranged on a container holding a drug. The drug is pressurised by a drive unit (not shown) and expelled through the micro nozzle in the form of Rayleigh droplet trains. The droplet trains are perturbed by air jets c impinging on the droplet trains such that coalescence of the droplets is reduced and an aerosol e, which may be inhaled by a user, is formed. An outer protective air flow f is also generated to prevent the droplets for the aerosol from depositing on an inside of a mouthpiece g. The protective air flow f passes through a porous filter h, to form a laminar air flow along the inside of the mouthpiece g. The filter is clamped between components of the mouthpiece g, or drive unit. Such an arrangement of a filter causes leak air flows which may reduce the quality of the aerosol by increasing coalescence, i.e. generating larger droplets, and/or increasing deposition on the inside surface of the mouthpiece g. Larger droplets and increased deposition are factors that both lead to a reduced quantity of the expelled dose reaching the desired target area, which is typically the deeper parts of the lungs for this type of inhaler.

As previously stated, it is an object of the present disclosure to improve on these and other aspects of aerosol dispensers.

Figure 2:
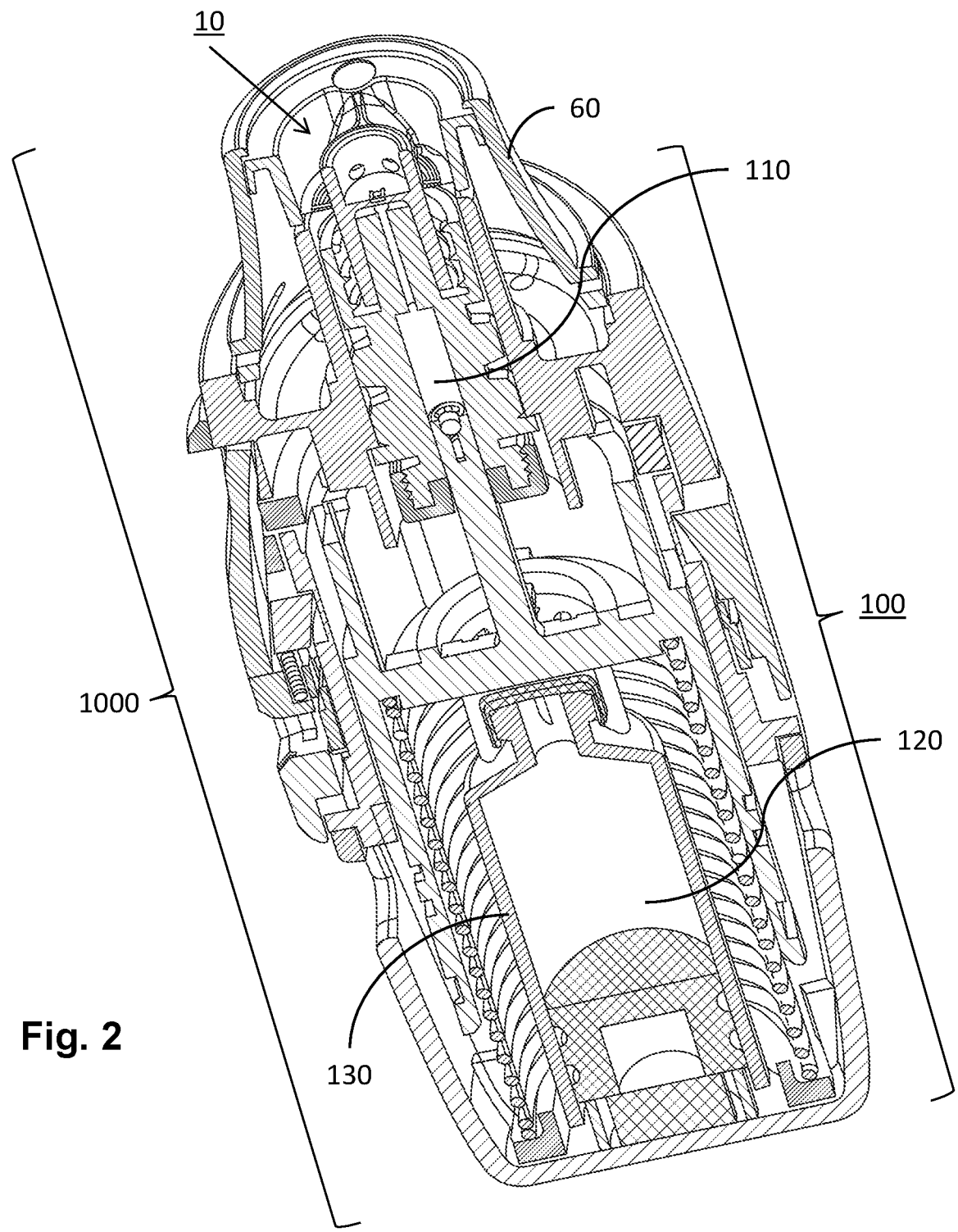
FIG. 2 shows a perspective cross-sectional view of an aerosol dispenser comprising an aerosol unit according to the present disclosure.

An aerosol dispenser 1000 is shown in FIG. 2. The aerosol dispenser 1000 comprises an aerosol unit 10 in accordance with the present disclosure, and a drive unit 100 arranged to pressurise a fluid product 120 in a chamber 110. The exemplified chamber 110 is a metered dose chamber of the aerosol dispenser 1000. As such, the fluid product 120 is stored in a primary container 130, from which a dose is metered by pumping it into the metered dose chamber 110 before being pressurised and expelled for dose delivery.

Although not shown in FIG. 2, it is also conceivable that the chamber 110 may be the primary container itself, which primary container may be pressurised to deliver the dose. In contrast to the exemplary embodiment of FIG. 2, the prior art device of shown in FIG. 1 is configured to pressurise the drug directly in the primary container.

The details of the drive unit 100 are not considered essential for the present disclosure, since many types of drive units may be used, as long as they may pressurise the fluid product in the chamber at 2-60 bars, as required in order to be able to generate Rayleigh droplet trains using a micro nozzle, as will be explained more in detail below. It suffices to note that the present aerosol unit 10 is easily adaptable to connect to different drive units and to different fluid product chambers. In the following description, the term "chamber 110" is meant to denote any fluid product-containing chamber, as outlined above, which may be pressurised to generate the aerosol.

The aerosol unit 10, which is the object of this disclosure, will now be described in more detail.

Figure 3:
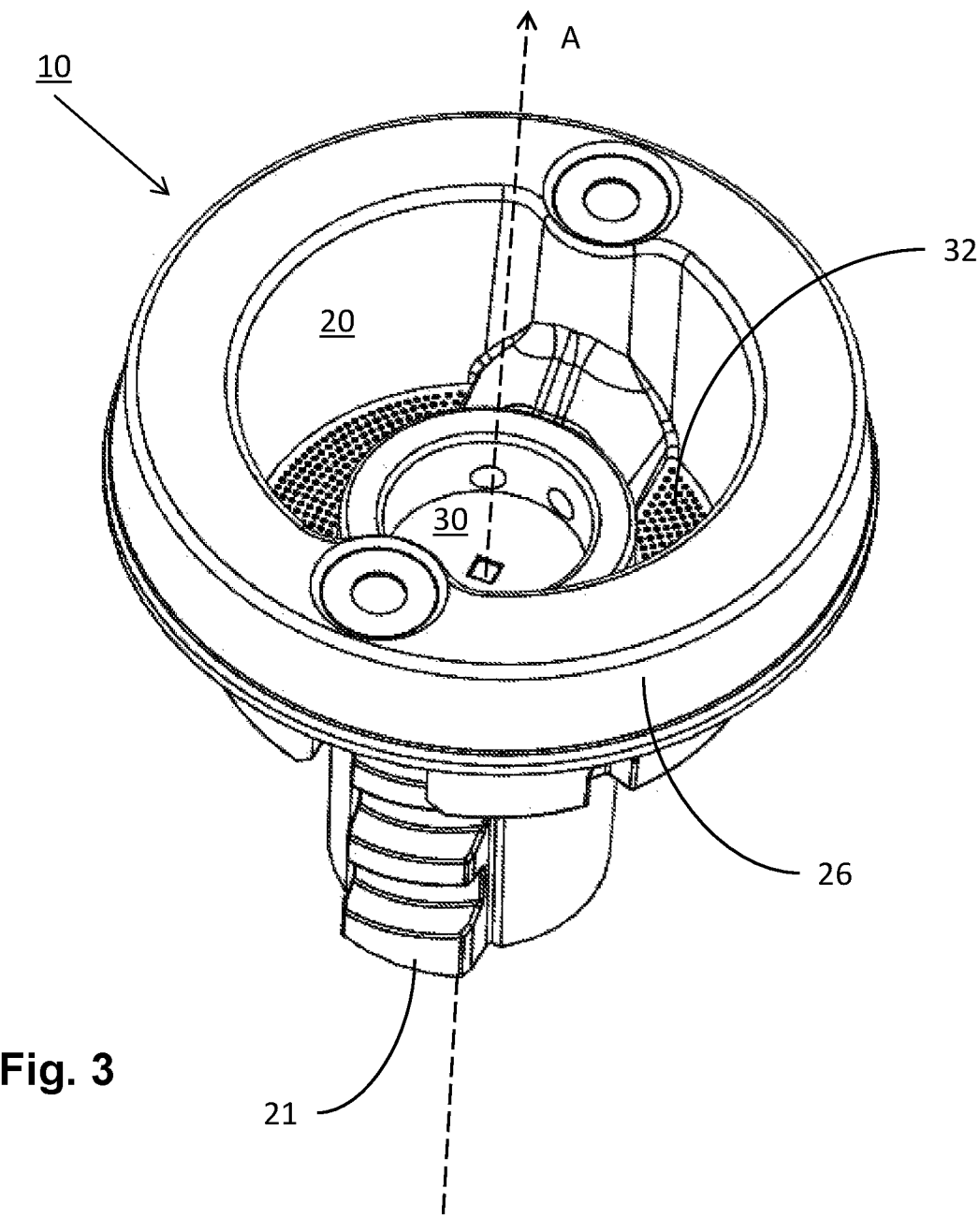
FIG. 3 shows a perspective view of an aerosol unit according to the present disclosure.

FIG. 3 shows a detailed perspective view of the aerosol unit 10 in relation to a longitudinal axis A. The aerosol unit 10 comprises an axially oriented body 20, having a distal inlet part 22 and a proximal outlet part 24. See FIG. 6. A nozzle carrier 30 is arranged in the body, between the inlet part 22 and the outlet part 24, transversally to the axis A. The nozzle carrier 30 is integrated in the body 20, e.g. moulded into the body 20, such that a contact surface between the nozzle carrier 30 and the body 20 forms an air-tight seal between the inlet part 22 and the outlet part 24. The nozzle carrier 30 furthermore comprises through-holes 32, which place the inlet part 22 in direct fluid communication with the outlet part, such as when the aerosol unit 10 is assembled with an aerosol dispenser 1000 or a drive unit 100.

The nozzle carrier 30 may comprise a carrier member 31 (FIG. 5) and a micro nozzle 35. The carrier member 31 may be an individual component of a thin sheet of material, which is assembled with the micro nozzle 35 prior to being placed in the moulding tool for injection moulding of the body 20 of the aerosol unit 10. Any suitable material may be used carrier member 31. Preferably, the carrier member 31 is formed out of thin sheet metal, e.g. steel, such as from a metal strip of steel. A metal sheet member allows accurate creation of the through holes 32 in the carrier member 31, such as by etching. Any additional configuration of shapes or structural features of the carrier member 31 are also simple to create, which structural features facilitate the integration of the nozzle carrier 30 in the aerosol unit 10 during moulding.

The inlet part 22 comprises first connecting elements 21 for connecting the aerosol unit to a chamber containing the fluid product 120. As illustrated in FIG. 3, the first connecting element 21 may be a luer lock coupling for connecting the aerosol unit to a primary package arranged with a corresponding coupling. The first connecting element 21 may alternatively be a luer slip coupling for friction fit with a primary package, or a thread, an O-ring, a gasket, a bayonet connection, or a cone-to-cone coupling, in order to provide a sealing connection under working pressure. As previously described, the first connecting element 21 may be configured to attach directly to a metered dose chamber 110.

The aerosol unit 10 further comprises a second connecting element 26 configured to connect the aerosol unit to a part of a drive unit 100 or to a part of an aerosol dispenser 1000, arranged to pressurise the fluid product 120 in the chamber, whether it is a primary package or a metered dose chamber. The second connecting element 26 may be customised to connect to any suitable drive unit 100 or aerosol dispenser 1000. For instance, the second connecting element may seal the aerosol unit against an outlet port, such as a mouthpiece of an inhaler 60 (FIG. 2), such that air inhaled by the user (in case of an inhaler) is channelled via the flow channels of the aerosol unit 10. Thereby, the aerosol unit 20 is versatile and adaptable, making its advantageous features available for a range of dispensers.

Figure 4:
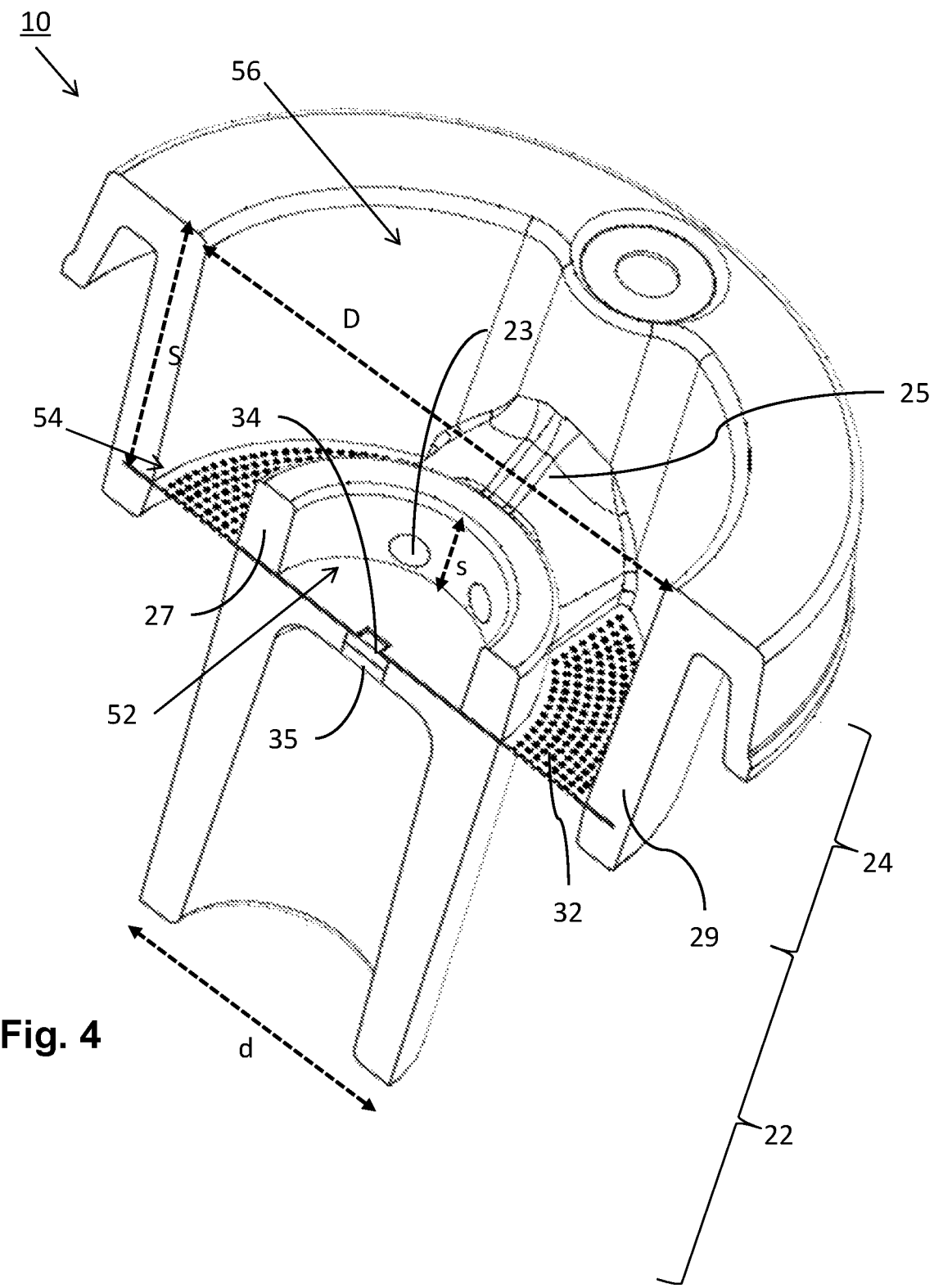
FIG. 4 shows a perspective cross-sectional view of an aerosol unit according to the present disclosure.
Figure 5:
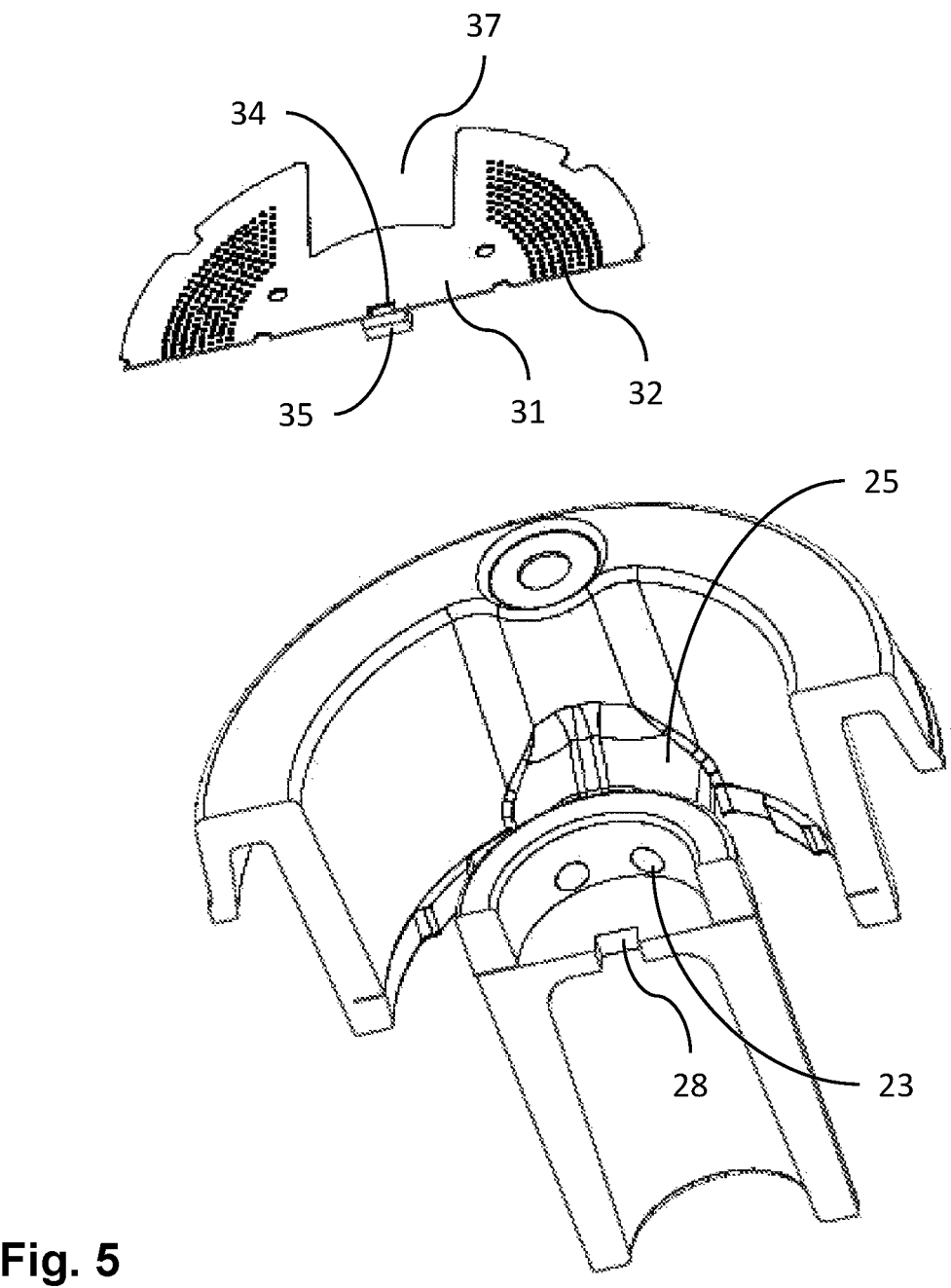
FIG. 5 shows an exploded perspective cross-sectional view of an aerosol unit according to the present disclosure.

FIGS. 4 and 5 show perspective cross-sectional views of the aerosol unit 30. FIG. 5 further shows an exploded view of the aerosol unit 10 comprising the body 20 and the nozzle carrier 30. As exemplified, the body 20 of the aerosol unit 10 may be tubular. The body 20 may be generally hollow in the axial direction, having an axial fluid flow passage. The distal inlet part 22 may comprise a first tubular part and the proximal outlet part 24 may comprise a second tubular part. The inlet part 22 and the outlet part 24 may be generally coaxially aligned. The second tubular part may have a larger inner diameter D than an outer diameter d of the first tubular part.

The nozzle carrier 30 may be generally disk-shaped and may be transversally arranged between the first tubular part and the second tubular part. The through-holes 32 of the nozzle carrier may be arranged in a circular pattern wherein an inner diameter of the circular pattern is larger than the outer diameter d of the first tubular part, and an outer diameter of the circular pattern is smaller than the inner diameter D of the second tubular part.

The nozzle carrier 30 may comprise a first opening 34. A micro nozzle 35 is mounted on the nozzle carrier 30. The micro nozzle 35 covers the first opening 34. Through-going orifices may be arranged in the micro nozzle 35 such that a pressurised fluid may be expelled through the micro nozzle 35, and through the first opening 34, in the form of a spray. Depending on the pressure and viscosity of the fluid, and on the dimensions of the orifices, the expelled fluid may form Rayleigh droplet trains at the first opening 34 on a proximal side of the nozzle carrier 30. For Rayleigh droplet train formation of the spray, the orifices may have diameters of 0.5-10 μm and the pressure of the fluid may be 2-60 bars.

The body 20 may comprise a second opening 28 which is aligned and adjacent with the first opening 34 of the nozzle carrier 30. The second opening 28 may accommodate the micro nozzle 35 by insert-moulding such that a flow passage is formed from the inlet part, through the second opening 28, the orifices of the micro nozzle 35 and the first opening 34, to the outlet part. The body 20 hermetically seals the micro nozzle 35 and the nozzle carrier 30 to the body 20. The inlet part 22 of the body 20 of the aerosol unit 10 may thus be attached to a chamber containing the fluid for spraying, whereby the fluid may be pressurised and expelled from the inlet part into the outlet part 24.

A turbulence structure 27 of the outlet part 24 extends proximally a distance s from the nozzle carrier 30. The turbulence structure 27 may radially surround, e.g. encircle, the second opening 28 such as to form a space around the first opening 34 of the nozzle carrier 30, hereinafter called inner fluid flow channel 52. The turbulence structure 27 is configured to comprise a turbulence port 23. The turbulence structure may be a wall element, as shown in the illustrated embodiment. Alternatively, the turbulence structure 27 may comprise structures such as protrusions, pillars, or other structures which may comprise the turbulence ports 23, which will be described below in more detail. If the turbulence structure comprises a plurality of structures, they are positioned so as to encircle the inner fluid flow channel 52. The inner fluid flow channel 52 is in fluid communication with the distal inlet part 22, via the micro nozzle 35. When connected to a pressurised chamber, such as a primary container or a metering chamber, spray in the form of Rayleigh droplet trains, may be expelled through the orifices of the micro nozzle 35 into the inner fluid flow channel 52. In the exemplified embodiment of FIGS. 4 and 5, the outer diameter of the turbulence structure 27 is generally equivalent to the outer diameter d of the first tubular part. However, other diameters of the turbulence structure 27 are possible.

A wall element 29 extends proximally. The wall element 29 is arranged radially outside the turbulence structure 27. A space is thus formed between the turbulence structure 27 and the wall element 29, which space is hereinafter named an outer fluid flow channel 54. The outer fluid flow channel 54 of the outlet part 24 is thus in fluid communication with the inlet part 22 via the through-holes 32 of the nozzle carrier. The outer fluid flow channel 54 is in fluid communication with ambient air, both with ambient air in the outer fluid flow channel 54 itself, and with ambient air at the inlet part 22, via the through-holes 32.

At a distance s from the nozzle carrier 30, i.e. at a proximal end of the turbulence structure 27, the inner fluid flow channel 52 and the outer fluid flow channel 54 merge into an outlet fluid flow channel 56. The through-holes 32 may be densely and evenly spaced between the turbulence structure 27 and the wall element 29 to generate a substantially homogeneous laminar fluid flow, e.g. air flow. The fluid (air) flow enters the outer fluid flow channel 54 via the through-holes 32. The carrier member 31, and the through-holes 32, serve to brake the speed of the flow of fluid (air) into the outer fluid flow channel 54 and to form the substantially laminar flow. The substantially laminar flow moves proximally into the outlet fluid flow channel 56. The substantially laminar fluid flow is part of a protective flow of the aerosol which serves to prevent droplets of the aerosol from depositing on the wall element, thereby enabling a greater portion of the expelled liquid product to exit the aerosol unit 10 and reach a pre-determined delivery site.

The aerosol unit 10 may furthermore comprise a turbulence duct 25. The turbulence duct 25 may extend from ambient air in the distal inlet part 22 of the aerosol unit or from ambient air radially outside the outer fluid flow channel 52. In the illustrated embodiment, the turbulence duct is a transversal duct from the wall element 29 to the turbulence structure 27. The turbulence duct 25 may comprise a covered flow channel from an exterior of the aerosol unit 10 to the inner fluid flow channel 52. The turbulence duct 25, e.g. the covered flow channel, opens into the inner fluid flow channel 52 through turbulence ports 23 comprised in the turbulence structure 27. The covered flow channel 25 places the inner fluid flow channel 52 in fluid communication with ambient air exterior of the aerosol unit 10. Since the turbulence ports 23 are moulded in the same step as the insert-moulding of the nozzle carrier 30 with the body 20 of the aerosol unit 10, the turbulence ports 23 may be accurately configured and directed with regard to the micro nozzle 35. This effect is due to a shorter tolerance chain of the moulded aerosol unit 10, as compared to prior art, where multiple separate components are assembled, which leads to longer tolerance chains.

Figure 6:
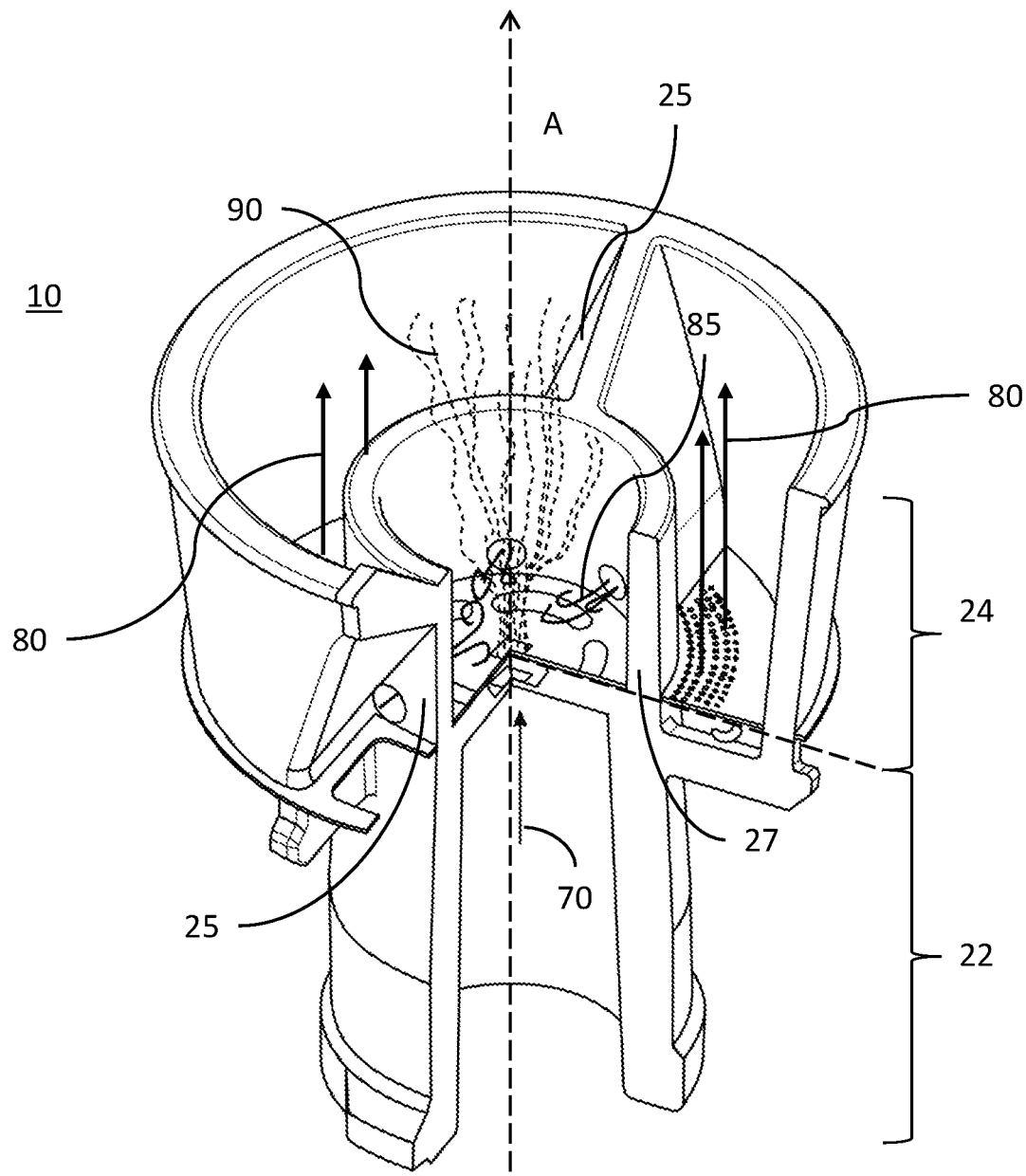
FIG. 6 shows a perspective cut-away view of an aerosol unit according to the present disclosure.

The covered flow channel 25 is "covered", i.e. shielded from the outer fluid flow channel 54 and the outlet fluid flow channel 56, to prevent air flowing through the covered flow channel 25 from disturbing the substantially laminar fluid flow in the outer fluid flow channel 54 and/or from disturbing a fluid flow in the outlet fluid flow channel 56. The covered flow channel 25 may have an aerodynamic shape configured to cause a fluid, entering the outer fluid flow channel 54 through through-holes 32, near the covered flow channel 25, to flow along its surface according to the coanda effect, thereby making the flow in the outer fluid flow channel 54 ring-shaped around the turbulence structure 27. One or more covered flow channels 25 may be arranged around the inner fluid flow channel 52. FIG. 6 illustrates an exemplary embodiment of the aerosol unit 10 comprising two covered flow channels 25 opening into the inner fluid flow channel 52 opposite each other.

Furthermore, the fluid flow of the through-holes 32 located near the turbulence structure 27 also experiences the coanda effect, causing the flow to adhere to the turbulence structure 27, thereby further increasing the ring-shaped characteristic of the flow. The part of the flow in the outer fluid flow channel 54, which is under the coanda effect, is generally not laminar.

The nozzle carrier 30 may be provided with a cut-out 37, aligned with the covered flow channel 25, to promote an air flow, from ambient surroundings, through the covered channel 25 to the inner fluid flow channel 52. The size and amount of the through-holes 32 of the nozzle carrier 30, and their layout, as well as the shape and size of the cut-out 37 and the turbulence duct 25 may be adapted to determine a percentage of the airflow that is used for turbulent flow and for the protective flow. These variables of the through-holes 32, cut-out 37 and turbulence duct 25 may also be used to improve and shape the flow in the outer fluid flow channel 54 and in the outlet fluid flow channel 56. The size, amount and layout of the through-holes 32 affect the laminar flow, the flow under the coanda effect and the general resistance of the flow. In one embodiment, the through-holes have diameters varying between of 0.1 mm and 0.17 mm. The c-c distance may be 0.24 mm. However, it is conceivable to have diameters ranging between 0.05 mm and 0.3 mm. The c-c distance could be 0.1 for smaller diameters.

An important aspect of the through-holes 32 is also to provide an appropriate flow resistance, for instance so that a user of an inhalation device in one breath draws in a suitable amount of air via the through-holes 32 when operating the device.

In use, the aerosol unit 10 is assembled with an aerosol dispenser 1000, or with a drive unit 100, as exemplified in FIG. 2, which shows that the proximal part 24 is configured to receive an outlet port 60, e.g. a mouthpiece, of the aerosol dispenser 1000. Alternatively, the proximal part 24 may be shaped as the outlet port 60, i.e. the proximal part 24 may be the outlet port 60 of the aerosol dispenser 1000.

A user wishing to expel a dose, positions the aerosol dispenser 1000 in an appropriate position and orientation, e.g. by placing the outlet port 60 of an inhaler in his/her mouth. Continuing the example of the aerosol dispenser 1000 as an inhaler, the user subsequently activates the drive unit 100 of the aerosol dispenser 1000 to pressurise the liquid product therein. Simultaneously, the user inhales through the outlet port 60. The liquid product is expelled from the chamber, through the orifices of the micro nozzle 35, and enters the inner fluid flow channel 52 in the form of a spray, as previously described. The pressure of the liquid product against the micro nozzle 35 is illustrated by the arrow 70 in FIG. 6.

Figure 7:
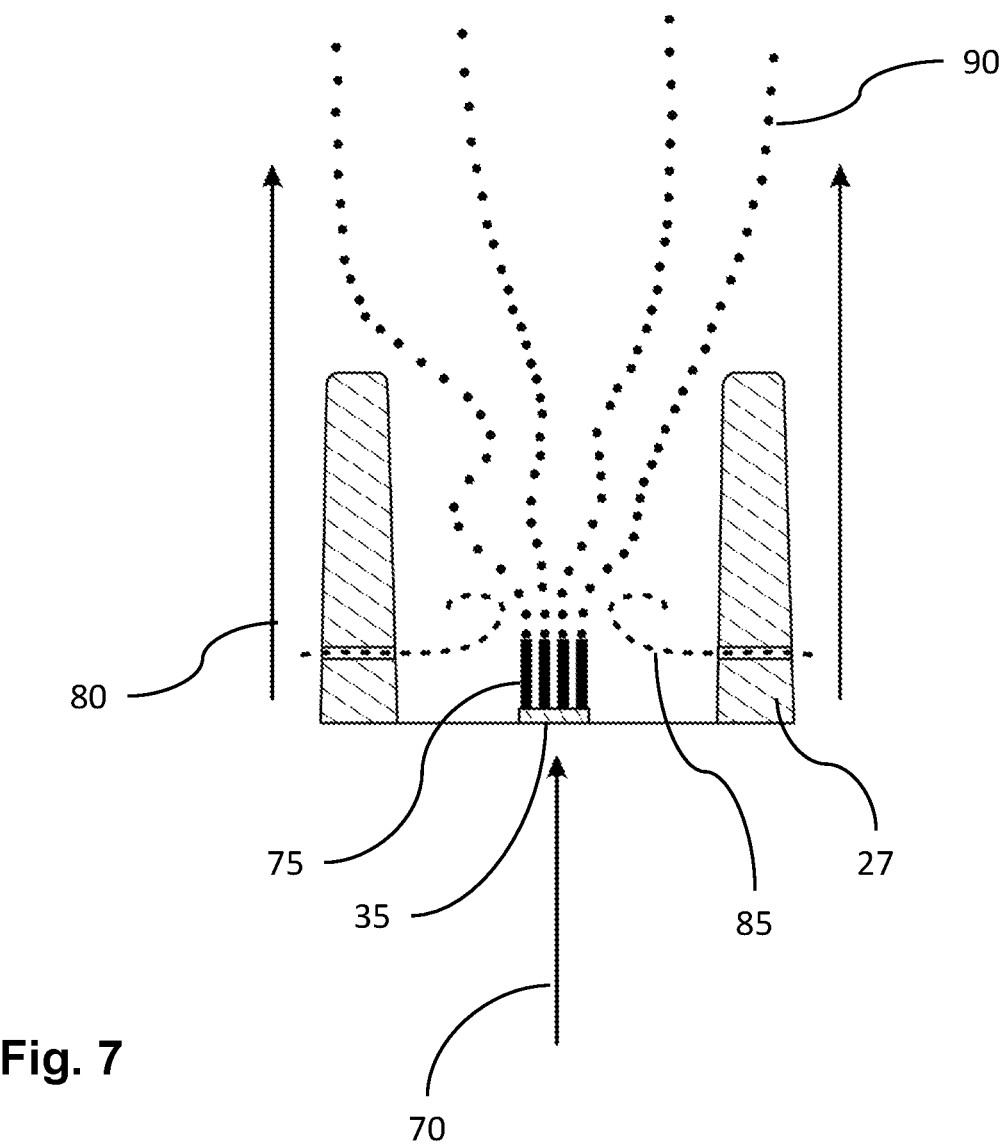
FIG. 7 shows a conceptual cross-sectional view of an aerosol unit according to the present disclosure.

As conceptually shown in FIG. 7, the liquid product is expelled through the micro nozzle 35 as liquid jets 75, which break up into droplets, which droplets preferably have a diameter of around 1 µm to 20 µm. Depending on the application of the aerosol dispenser the dimensions of the orifices of the micro nozzle are suitably adapted. In the exemplary case of an inhalation device, the droplets need to be 2-5 µm for local delivery to the lungs, whereas systemic delivery into the body, beyond the lungs, requires droplet diameters of 0.1-2 µm.

The droplets form into Rayleigh droplet trains. However, due to friction with air, the droplets at the head of the droplet trains tend to lose speed and coalesce with droplets approaching from behind. To prevent coalescence and to control droplet size, the droplet trains need to be broken up.

At the same time, ambient air is drawn into the aerosol unit 10 by the inhalation of the user. The air is separated into a protective flow 80 which enters the outer fluid flow channel 54 via the through-holes 32, and a turbulent flow 85 which enters the inner fluid flow channel 52 via the covered flow channels 25 and the turbulence ports 23. The turbulent flow 85 serves to break up the droplet trains and to separate the droplets such that a mix of turbulent air and droplets form an aerosol 90. The aerosol 90 is carried proximally towards the outlet flow channel 56 together with the air inhaled by the user. The turbulence structure 27, around the inner fluid flow channel 52, serves to shield the formation process of the aerosol from the laminar flow 80 until the droplets are properly mixed with air. When the aerosol enters the outlet fluid flow channel 56, the laminar flow, e.g. laminar air flow, serves to prevent the droplets of the aerosol from depositing on the wall element 29.

As discussed previously, the insert-moulding of the nozzle carrier 30 in the body 20 of the aerosol unit is advantageous because it eliminates leakage air flows at interfaces between components, which leakage air flows might disturb the laminar flow 80 or the turbulent flow 85. The leakage flows are eliminated because the interfaces between the nozzle carrier 30 and the body 20 of the aerosol unit become hermetically sealed in the moulding process.

Using a metal, e.g. steel, sheet for the carrier member of the nozzle carrier 30 also enables very accurate formation of the through-holes 32, e.g. by etching the carrier member. The through-holes 32 may then be used to direct the laminar flow 80 to increase the protective properties of the laminar flow 80 and to ensure that a larger portion of the expelled liquid product may reach a delivery target.

The insert-moulding of the nozzle carrier 30 further reduces the effect of tolerances on the accuracy of the various flows, because the tolerance chains of the integrated aerosol unit 10 are shorter, as compared to a prior art device assembled from multiple separate components. This allows an the engineered accuracy and effect of, for instance, the through-holes 32 and the turbulence ports 23 to achieve a greater effect since accuracy of the generated flows is not reduced by component mis-match.

Figure 8:
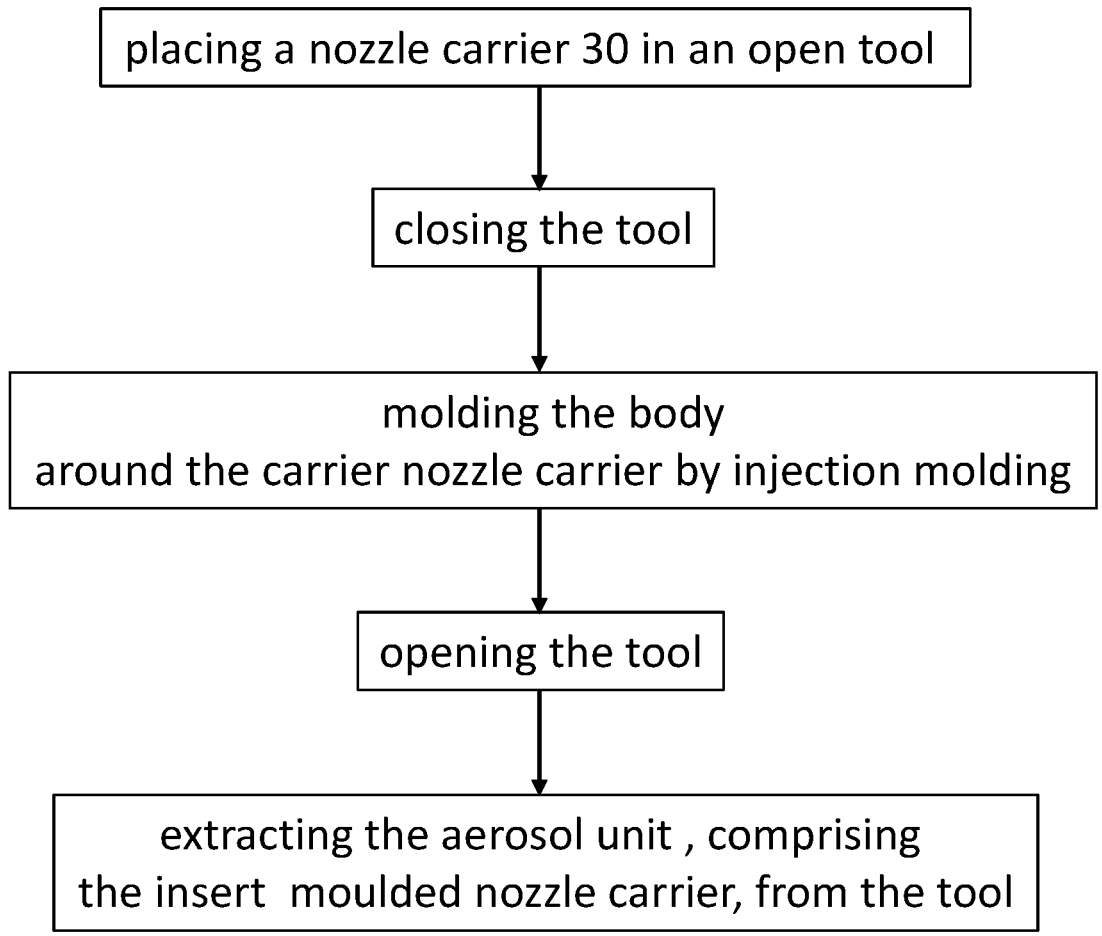
FIG. 8 shows a flow chart of the method of integrating a nozzle carrier in an aerosol unit according to the present disclosure.

As generally outlined in FIG. 8 the moulding process of the aerosol unit comprises generally the following steps:

fixating a nozzle carrier 30 comprising a micro nozzle 35 in a tool comprising a first tool part comprising first sliders closing the tool with a second tool part comprising second sliders moulding the body 20 around the nozzle carrier 30 by injection moulding opening the second sliders opening the tool open the first sliders to extract the aerosol unit 10 comprising the insert-moulded nozzle carrier 30 from the tool

The invention claimed is:

1. An aerosol unit for an aerosol dispenser, the aerosol unit comprising:

an axially oriented body, having a distal inlet part and a proximal outlet part; and a carrier member arranged in the body, transversally to the axis between the inlet part and the outlet part, wherein the carrier member comprises through-holes which place the inlet part in fluid communication with the outlet part, wherein the carrier member is insert-moulded into the body such that a contact surface between the carrier and the body forms an air-tight seal, and wherein the outlet part comprises an outer fluid flow channel and an inner fluid flow channel, wherein the outer fluid flow channel and the inner fluid flow channel are coaxially arranged, and wherein a turbulence structure extends proximally a distance from the carrier member, between the inner fluid flow channel and the outer fluid flow channel.

2. The aerosol unit according to claim 1, wherein the carrier member comprises a micro nozzle mounted on the carrier member.

3. The aerosol unit according to claim 1, wherein the carrier member is formed of a sheet metal member.

4. The aerosol unit according to claim 2, wherein the micro nozzle is aligned with the inner fluid flow channel and places the inner fluid flow channel in fluid communication with the distal inlet part.

5. The aerosol unit according to claim 1, wherein the through-holes are located radially outside the turbulence structure.

6. The aerosol unit according to claim 1, wherein the outer fluid flow channel and the inner fluid flow channel merge at a proximal end of the turbulence structure to form an outlet fluid flow channel.

7. The aerosol unit according to claim 5, wherein the proximal part is configured to receive an outlet port of an aerosol dispenser.

8. The aerosol unit according to claim 5, wherein the proximal part is an outlet port of an aerosol dispenser.

9. The aerosol unit according to claim 2, wherein the inlet part comprises a first connecting element for connecting the aerosol unit to a chamber containing a fluid product, wherein the fluid product is configured to be pressurised in the chamber and expelled through the micro nozzle as a spray.

10. The aerosol unit according to claim 9, wherein the chamber is a metered dose chamber of an aerosol dispenser.

11. The aerosol unit according to claim 9, wherein the first connecting element is a luer lock coupling, a luer slip coupling, a thread, an O-ring, a gasket, a bayonet coupling or a cone-to-cone coupling for a liquid-tight seal between the aerosol unit and a primary package under working pressure.

12. The aerosol unit according to claim 1, wherein the aerosol unit comprises a turbulence duct comprising a covered flow channel from ambient air exterior of the aerosol unit to the inner fluid flow channel.

13. The aerosol unit according to claim 12, wherein the turbulence duct opens into the inner fluid flow channel through turbulence ports comprised in the turbulence structure.

14. An aerosol dispenser comprising the aerosol unit according to claim 1.

15. The aerosol unit according to claim 2, wherein the distal inlet part comprises a connecting element configured to connect the aerosol unit to a metered dose chamber of an aerosol dispenser containing a fluid product such that pressurization of the fluid product expels the fluid product through the micro nozzle as a spray.

16. An aerosol unit for an aerosol dispenser, where the aerosol unit comprises:

an axially oriented body having a distal inlet part and a proximal outlet part aligned along a longitudinal axis;

a metal carrier member separating the distal inlet part from the proximal outlet part and comprising through-holes, where the carrier member is insert-moulded into the body transversally to the longitudinal axis to form an air-tight seal between the distal inlet part and the proximal outlet part; and a micro nozzle associated with the carrier member configured to allow a pressurised fluid product to be sprayed, wherein through-holes provide fluid communication between the distal inlet part and the proximal outlet part, and wherein the proximal outlet part comprises an outer fluid flow channel and an inner fluid flow channel, where the outer fluid flow channel and the inner fluid flow channel are coaxially arranged.

17. The aerosol unit according to claim 16, wherein a turbulence structure extends proximally a distance from the carrier member to separate the inner fluid flow channel and the outer fluid flow channel, wherein the through-holes are located radially in the outer fluid channel.

18. The aerosol unit according to claim 17, wherein the micro nozzle is in fluid communication with both the inner fluid flow channel and the distal inlet part.

* * * * *